(12) United States Patent
Shavit

(10) Patent No.: US 9,579,205 B2
(45) Date of Patent: Feb. 28, 2017

(54) LINERS FOR MEDICAL JOINT IMPLANTS WITH IMPROVED WEAR-RESISTANCE

(71) Applicant: Ronen Shavit, Tel Aviv (IL)

(72) Inventor: Ronen Shavit, Tel Aviv (IL)

( * ) Notice: Subject to any disclaimer, the term of this patent is extended or adjusted under 35 U.S.C. 154(b) by 0 days.

(21) Appl. No.: 14/482,431

(22) Filed: Sep. 10, 2014

(65) Prior Publication Data

US 2015/0073560 A1    Mar. 12, 2015

Related U.S. Application Data

(60) Provisional application No. 61/876,770, filed on Sep. 12, 2013.

(51) Int. Cl.
*A61F 2/30* (2006.01)
*A61L 27/44* (2006.01)

(52) U.S. Cl.
CPC ........ *A61F 2/30767* (2013.01); *A61L 27/443* (2013.01); *A61L 27/446* (2013.01); *A61L 2400/12* (2013.01); *A61L 2430/24* (2013.01)

(58) Field of Classification Search
CPC ................ A61F 2/34; A61F 2002/3084; A61F 2002/30003
See application file for complete search history.

(56) References Cited

U.S. PATENT DOCUMENTS

| | | | |
|---|---|---|---|
| 4,535,486 A | 8/1985 | Roberts et al. | |
| 5,480,448 A | * 1/1996 | Mikhail | A61F 2/34 623/22.24 |
| 5,976,190 A | 11/1999 | Anhalt et al. | |
| 6,390,992 B1 | 5/2002 | Morris et al. | |
| 6,566,451 B2 | 5/2003 | Wang et al. | |
| 6,686,437 B2 | 2/2004 | Buchman et al. | |
| 6,709,463 B1 | 3/2004 | Pope et al. | |
| 6,966,932 B1 | 11/2005 | Schroeder | |
| 7,811,486 B2 | 10/2010 | Karim et al. | |

(Continued)

FOREIGN PATENT DOCUMENTS

CN    101396571    * 4/2009
CN    101396571 b    * 4/2013

(Continued)

OTHER PUBLICATIONS

Kurtz et al. "PEEK Biomaterials in Trauma, Orthopedic, and Spinal Implants." *Biomaterials*. Nov. 2007, 28(32):4845-4869—http://www.ncbi.nlm.nih.gov/pmc/articles/PM2040108.

Kinbrum. "Taking a PEEK at Material Options for Orthopedics." 2009. http://www.mdtmag.com/articles/2009/01/taking-peek-material-options-orthopedics.

(Continued)

*Primary Examiner* — Thomas J Sweet
*Assistant Examiner* — Daniel Bissing
(74) *Attorney, Agent, or Firm* — Merchant & Gould P.C.

(57) ABSTRACT

A polymeric liner for joint implants includes at least one friction reducing member and at least one body member. The friction reducing member is made of a polymeric matrix which contains a polymeric material and at least one nanotube nanoparticle having a volume concentration of between 5%-99% v/v (volume per volume). The body member is formed of at least a polymeric material. The friction reducing member and the body member are conjoined preferably by compression molding or any other method of coupling such as mold injection, 3D printing, adhesion or any other suitable method can be applied. A method produces the polymeric.

12 Claims, 6 Drawing Sheets

(56) References Cited

U.S. PATENT DOCUMENTS

| | | |
|---|---|---|
| 8,257,835 B2 | 9/2012 | Jani et al. |
| 2007/0140607 A1* | 6/2007 | Lee .................... F16C 9/04 384/206 |
| 2008/0071381 A1 | 3/2008 | Buscher et al. |
| 2008/0081061 A1 | 4/2008 | King et al. |
| 2009/0032499 A1* | 2/2009 | Tenne ................ A61C 7/14 216/109 |
| 2009/0234459 A1* | 9/2009 | Sporring ........... A61L 27/446 623/18.11 |
| 2011/0039014 A1 | 2/2011 | King et al. |
| 2011/0166671 A1* | 7/2011 | Kellar .............. A61F 2/30767 623/23.53 |
| 2011/0282451 A1 | 11/2011 | Sporring et al. |
| 2014/0135938 A1* | 5/2014 | Assell ............... A61F 2/3872 623/20.31 |

FOREIGN PATENT DOCUMENTS

| | | |
|---|---|---|
| EP | 2075014 | 7/2009 |
| EP | 1882483 | 3/2011 |
| WO | WO 96/41068 | 12/1996 |
| WO | WO 2006/088480 | 8/2006 |
| WO | WO 2009/115790 | 9/2009 |

OTHER PUBLICATIONS

Website for Dictronite—Technical Overview Section and Brochure—http://www.dictronite.com/index.php/en/—retrieved Sep. 10, 2014.

International Search Report for PCT/IL2014/000047, mailed Nov. 20, 2014.

International Preliminary Report on Patentability for PCT/IL2014/000047, mailed Mar. 15, 2016.

* cited by examiner

LINERS FOR MEDICAL JOINT IMPLANTS WITH IMPROVED WEAR-RESISTANCE

This application claims benefit of U.S. Provisional Ser. No. 61/876,770, filed 12 Sep. 2013 and which application is incorporated herein by reference. To the extent appropriate, a claim of priority is made to the above disclosed application.

FIELD OF THE DISCLOSED TECHNIQUE

The disclosed technique relates to liners for medical joint implants, in general, and to liners with improved wear-resistance for medical joint implants, in particular. The disclosed technique further relates to methods for manufacturing a polymeric liner with improved wear-resistance.

BACKGROUND OF THE DISCLOSED TECHNIQUE

A natural joint is a connection between two bones and is classified under two broad categories: (i) joints lacking a joint cavity which allow little or no movement, such as the joint between adjacent vertebrae; and (ii) joints having a joint cavity which allow free movement of such joints in the body. These joints are called synovial joints or synovial-type joints. In humans, common synovial joints include the hip joint, the knee joint, the ankle joint, the shoulder joint, the elbow joint, the wrist joint, the finger joint, the finger metacarpal joint, the toe joint, the toe-metatarsal joint and the carpometacarpal joint. Synovial-type joints can be further classified into three categories: uniaxial, biaxial and triaxial. Uniaxial joints can be further categorized into hinge and pivot joints. Examples of hinge joints are the joints of the fingers, known as the interphalangeal joints. Pivot joints are formed by a central bony pivot surrounded by an osteo-ligamentous ring. Movements are permitted in one plane around a vertical axis. Examples of this type of joint are the superior and inferior radioulnar joints (i.e., joints of the elbow) and the median atlantoaxial joint (i.e., upper neck joints). In a biaxial joint, motion occurs in two planes; thus permitting two degrees of freedom. There are two types of biaxial joints, saddle joints and condyloid joints. An example of a saddle joint is the carpometacarpal joint of the thumb, where the bones fit together resembling an individual riding a horse while sitting on a saddle, with one bone being concave and the other being convex. Examples of condyloid joints are the metacarpophalangeal joints of the fingers. Triaxial joints have three degrees of motion and permit movement in three planes. There are two types of triaxial joints, ball and socket joints, and plane joints. Examples of ball and socket joints include the shoulder joint and the hip joint.

FIGS. 1-4 illustrate artificial joint implants according to the prior art. These joint implants are presented herein in order to facilitate understanding of the field of the disclosed technique. Reference is made to FIG. 1, which is an exploded side perspective view of a total hip replacement implant, as is known in the prior art. Total hip replacement implant 10 includes a cup 11, a liner 12 and a stem 13. Stem 13 includes a head 14. Hip replacement implant 10 can be categorized as a ball-and-socket joint, i.e., one in which the rounded surface of head 14 fits into and moves within a cup-shaped depression of liner 12 which fits into cup 11. Such a ball-and-socket joint allows freedom of movement up, down, right, left and in a full 360-degrees of rotation.

Reference is now made to FIG. 2, which is an example of a total knee replacement implant, generally referenced 20, as is known in the prior art. The knee joint is a pivotal hinge joint which permits flexion and extension as well as a slight medial and lateral rotation. Total knee replacement implant includes a head 21, a liner 22 and a stem 23. Head 21 is coupled with liner 22 which is coupled with stem 23. Reference is now made to FIG. 3 which is a side perspective view of a total disc replacement implant, generally referenced 30, as is known in the prior art. Total disc replacement implant includes a top plate 31, a liner 32 and a base plate 33. Reference is now made to FIG. 4 which is a total ankle replacement implant, generally referenced 40, as is known in the prior art. Total ankle replacement implant 40 includes a top plate 41, a liner (or insert) 42 and a base plate 43.

Common materials which have been used over the years for medical joint implants are: metals, ceramics, polymers and composite materials. Different types of medical joint implants include metal-on-metal implants, which are made of stainless steel or cobalt chrome alloys, ceramic-on-ceramic implants, which are made of zirconia and alumina, polymer implants such as Ultra-High-Molecular-Weight Polyethylene (UHMWPE) and polyimides, and composite material implants such as carbon fiber-reinforced PEEK (polyether ether ketone).

Metal-on-metal joint implants as well as ceramic and UHMWPE joint implants each suffer from a common drawback, viz. mechanical wear and degradation of the implant in a patient's body due to the repetitious movement of one part of the implant in respect of the other part of the implant. For example, in 2010, there was a great deal of publicity in the USA on the failure and recall of the metal-on-metal hip marketed by DePuy. The recall came after data from a study indicated that the five year failure rate of this metal-on-metal hip is approximately 13%. Even if the defective device is replaced, it can leave behind dangerous, possibly deadly fragments that may not be discovered for years. DePuy identified reasons for the failure of the hip replacement system as component loosening, component malalignment, infection, fracture of the bone, dislocation, metal sensitivity and pain. In general, with respect to all metal-on-metal artificial joints, the movement of the metal head within the metal cup of the joint implant results in a high volume of metallic debris which is absorbed into the patient's body. The absorption of metallic debris by the body can cause inflammatory reactions, resulting in pain in the groin area, death of tissue in the hip joint and actual loss of surrounding bone. Polymer joint implants suffer from similar drawbacks with respect to degradation and wear debris. Every year, more than a million Americans receive an artificial hip or knee prosthesis. Such joint implants are designed to last years but in about 15-20 percent of patients who receive a total joint replacement, the joint implant prematurely loosens and has to be replaced early, which can cause dangerous complications in patients, in particular in elderly patients. Over the years the durability of artificial joint implants has improved, for example a hip implant now lasts between 10-15 years and a knee implant lasts between 7-10 years, yet the average age of patients in need of an artificial prosthesis has significantly lowered. Moreover, as active participation in sports, both recreational and professional, is an increasing reality for a significant number of younger patients, there is a growing need for a durable joint implant which exhibits a higher lasting rate.

As friction is a major cause of tear and wear of joint implants, attempts to provide durable joint implants aim at developing new ceramic or composite materials having a higher wear resistance and a lower friction coefficient. One attempted solution to overcome the accelerated wear of joint implants due to the continuous friction of non-lubricated surfaces of the joint implant was made by coating one or both of the contacting surfaces with films of hydroxyapatite, thus reducing the coefficient of friction between the contacting surfaces. Such films however end up being quite thick and unstable, and tend to break off from the joint implant.

Many examples of attempts to overcome the accelerated wear of joint implants are known. U.S. Pat. No. 5,976,190 to Klaus-Peter Anhalt et al., entitled "Orthopaedic connection" is directed to an orthopedic clamp connection as a functional element for force transmission in a prosthesis comprising a tube socket and a tube made of light metal, and a contact area there between. The contact area includes an intermediate layer comprising a low molecular weight carrier material in which at least one of a lubricant or an auxiliary is embedded. The carrier material is selected from inorganic materials such as metal, metal salt, metal oxide or ceramic material. The intermediate layer has a thickness from 0.1 µm to 1 mm. Suggested lubricants are a dicarboxylic ester, a fatty acid, a fatty acid ester, a fatty acid amide, a metal soap, a silicone oil, molybdenum sulfide, a polyolefin wax, a paraffin, a fluoropolymer or a combination thereof.

PCT International Application Publication No. WO 2009/115790 to Peter White, entitled "Replacement bone joint" is directed to a replacement bone joint that has joint members such as a femoral prosthesis and an acetabular prosthesis which define a ball and socket joint between a head and a titanium cup. The titanium cup has a lining and the head, which is made of stainless steel, is provided with an adhered coating. The coating and lining are formed from a non-crossed-linked thermoplastic material such as nylon, which may be incorporated with lubricants such as silicone, hydrogels, molybdenum sulfide, polyvinyl pyrollidone, glycerin, mineral oil grease and/or graphite.

SUMMARY OF THE PRESENT DISCLOSED TECHNIQUE

The prior art provides for thin film coatings which are adhered to the contacting surfaces of a metal joint in order to reduce the coefficient of friction in joint implants. A major drawback of such coatings is that such thin film coatings which are exposed to continual rubbing tend to chip off prematurely, leaving the base material bare and prone to degradation. Such thin film coatings have not prolonged the durability of joint implants in a significant manner. The prior art does not provide a solution that enhances wear resistance and the durability of joint implants. According to the disclosed technique, the wear debris of a joint implant is significantly reduced, thus providing numerous advantages. For example, by reducing the wear debris produced by friction from a damaged implant, the disclosed technique enables the postponement of repeated surgery for replacing a damaged joint implant. In addition, a reduction of friction may also assist in the reduction of component loosening due to excessive loads applied on an articulated joint, for instance, acetabular component loosening in a total hip replacement.

In accordance with the disclosed technique, there is thus provided a polymeric liner for joint implants which includes at least one friction reducing member and at least one body member. The friction reducing member is made of a polymeric matrix which contains a polymeric material and at least one nanotube nanoparticle having a volume concentration of between 5%-99% v/v (volume per volume). The body member is formed of at least a polymeric material. The at least one friction reducing member includes at least one outer surface and at least one inner surface. The at least one body member includes at least one inner surface conjoined with the at least one friction reduction member inner surface. The friction reducing member and the body member are conjoined preferably by compression molding. However, any other method of coupling such as mold injection, 3D printing, adhesion or any other suitable method can be applied. At least one friction reducing member is positioned on a surface area of the polymeric liner which is in contact with a moving part of the joint implant. Specifically, at least one outer surface of the friction reducing member is in contact with a moving part of the joint implant. In an embodiment of the disclosed technique, the friction reducing member forms an outer skin of a polymeric matrix which includes a polymeric material and at least one organic or inorganic nanotube nanoparticle having a volume concentration of between 5%-99% v/v. This outer skin substantially covers the body member.

In a further embodiment of the disclosed technique the friction reducing member and the body member are prepared from a polymeric material and at least one nanoparticle selected from nanotube nanoparticles of tungsten disulfide ($WS_2$) or molybdenum disulfide ($MoS_2$) having a volume concentration of between 5%-99% v/v.

According to a further aspect of the disclosed technique there is thus provided a method of production of a polymeric liner for joint implants. The method comprises the procedures of providing a mold with a cavity in a shape of the polymeric liner, applying a first layer made of a polymeric matrix in the cavity of the mold, wherein the first layer contains a polymeric material and at least one nanotube nanoparticle having a volume concentration of between 5%-99% v/v. This first layer forms the friction reducing member. Thereafter, a second layer of at least a polymeric material is applied on the first layer of the polymeric matrix. The second layer forms a body member made of at least a polymeric material. The mold is then closed and heated with the polymeric material to a temperature below the melting point of the polymeric material. Pressure is applied to the mold such that air contained in the mold is sucked out and the polymeric material forms in the shape of the polymeric liner. Finally, the mold is opened and the polymeric liner is removed from the mold. The resulting polymeric liner comprises a friction reducing member and a body member which are conjoined by compression molding.

In another embodiment of the disclosed method of production, before the procedure of closing the mold, a third layer of polymeric matrix may be applied on the second layer. This third layer contains a polymeric material and at least one nanotube nanoparticle having a volume concentration of between 5%-99% v/v. The resulting polymeric liner according to this embodiment is composed of a skin made of homogeneously distributed nanotube nanoparticles in a polymeric matrix and a body member made of a polymeric material. Preferably, the resulting skin should substantially cover the body member.

In an additional embodiment of the disclosed method of production the at least one nanotube nanoparticle is selected from nanotube nanoparticles of tungsten disulfide ($WS_2$) or molybdenum disulfide ($MoS_2$), either one having a volume concentration of between 5%-99% v/v. A further embodiment of the disclosed method of production includes the procedures of providing a mold with a cavity in a shape of the polymeric liner and loading a required amount of a polymeric matrix into the cavity, wherein the polymeric matrix includes a polymeric material and a nanotube nanoparticle having a volume concentration of between 5%-99% v/v. The mold with the polymeric matrix is then heated to a temperature below the melting point of the polymeric material. Pressure then is applied to the mold such that air contained in the mold is sucked out and the polymeric material forms in the shape of the polymeric liner. Finally, the mold is opened and the joint implant is removed from the mold. The resulting polymeric liner is thus composed of homogeneously distributed nanotube nanoparticles in a polymeric matrix.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a wear resistant polymeric liner for joint implants. The polymeric liner disclosed herein can be manufactured for use in medical joint implants such as a hip joint, a knee joint, an ankle joint, an intervertebral disc, a shoulder joint, an elbow joint, a wrist joint, a finger joint, a finger metacarpal joint, a toe joint, a toe-metatarsal joint, a carpometacarpal joint and the like. In addition, the polymeric liner of the disclosed technique can also be used in other types of medical implants (such as, intramedullary nails, where UHMWPE washers are used to eliminate interlocking screw movement relative to the nail implant) where an enhanced wear resistance and long durability of the implant is required. The description herein of the disclosed technique as it relates to polymeric liners for joint implants such as hip and knee implants should be viewed as merely an example of the uses of the disclosed technique. The disclosed technique relates to any situation where artificial joints are used and is not limited to artificial joints used in humans.

Figure 1:
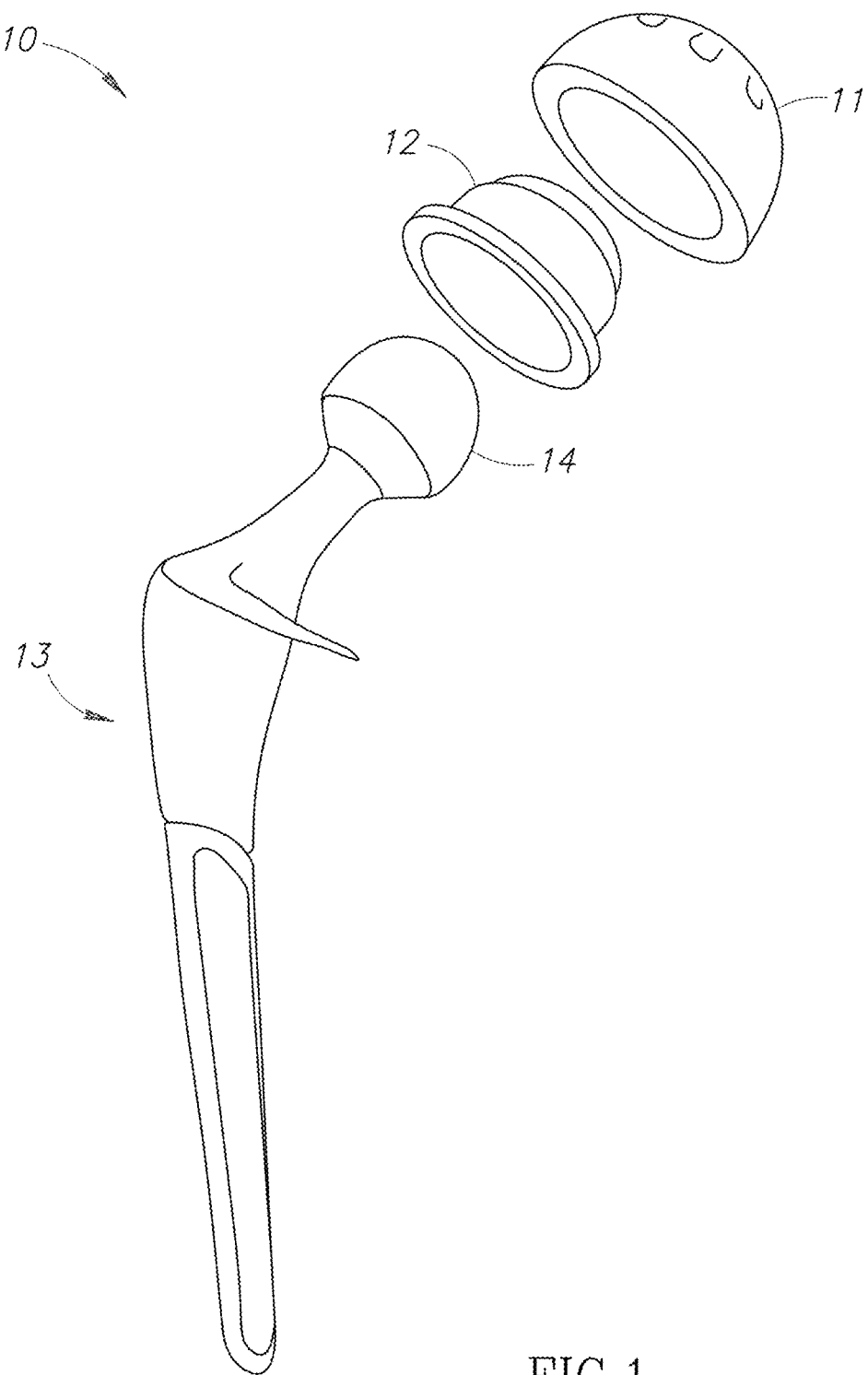
FIG. 1 is an exploded side perspective view of a total hip replacement implant, as is known in the prior art.
Figure 2:
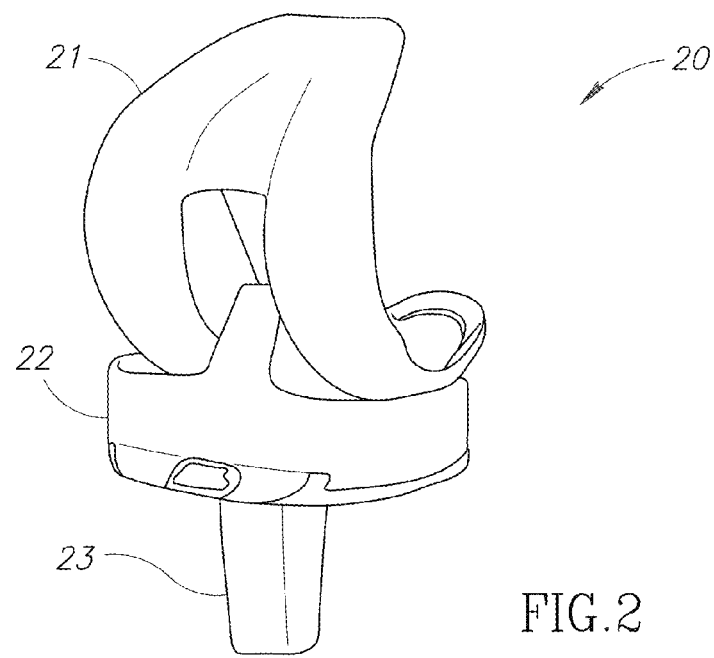
FIG. 2 is a side perspective view of a total knee replacement implant, as is known in the prior art.
Figure 3:
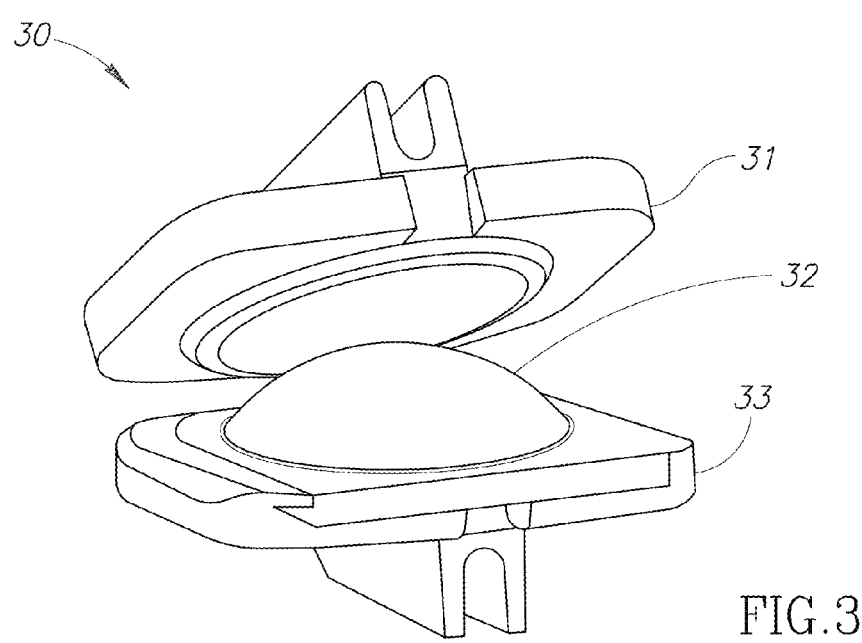
FIG. 3 is a side perspective view of a total disc replacement implant, as is known in the prior art.
Figure 4:
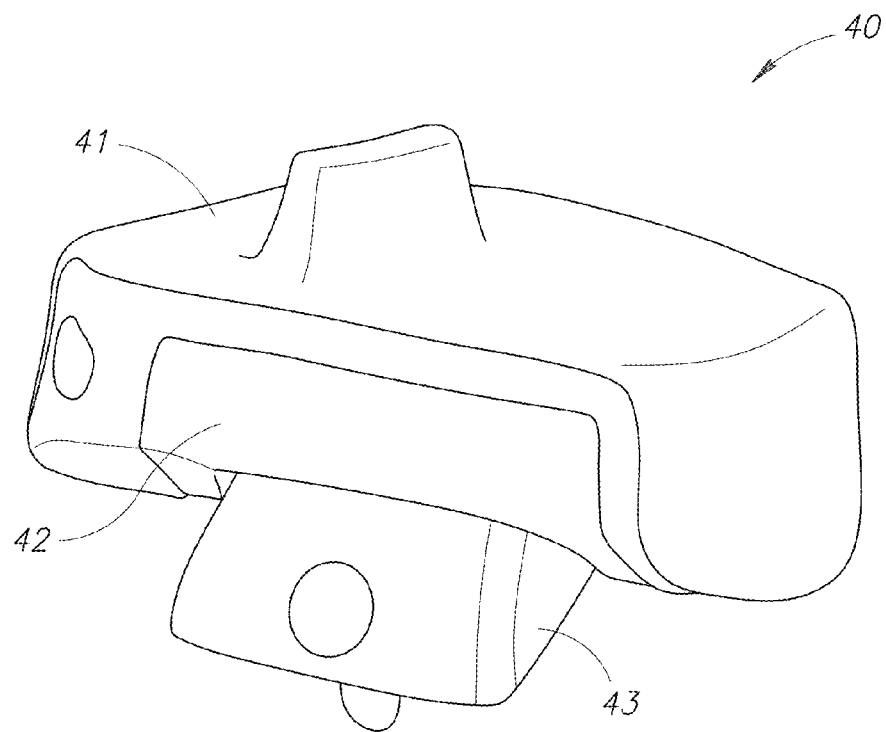
FIG. 4 is a side perspective view of a total ankle replacement implant, as is known in the prior art.

A polymeric liner for a medical joint implant is constructed to be engaged in between a head (or a top plate) and a stem (or a base plate) of a medical joint implant. The polymeric liner has two contacting surfaces constructed to closely contact the bottom surface of the head (or top plate) from one side and the upper surface of the stem (or base plate) from the other side. In particular, the two contacting surfaces of the polymeric liner are located at the friction areas. For example, in reference to FIG. 1, polymeric liner 12 is positioned between the bottom surface of head 11 and the upper surface of stem 14 thus reducing the friction between the contacting surfaces of head 11 and stem 14, if positioned one (head) in contact with the other (stem) without a liner.

The terms "medical implant," "prosthesis," "artificial implant," "polymeric implant," "replacement implant," "joint implant" and "medical joint" are used interchangeably throughout the description and refer to artificial joints. The term "polymeric matrix" herein refers to a polymer material composed of at least one nanotube nanoparticle, which is used as a liner or a bearing between two hard surfaces such as metals and/or ceramics to reduce friction between two adjacent moving components. The term nanoparticle within the context of the disclosed technique refers to a microscopic particle with at least one dimension (length, width and/or thickness) less than 100 nanometers (herein abbreviated nm). The term nanotube refers to a nanometer-scale tube-like structure. Examples of nanoparticles having a nanotube configuration which are useful in the disclosed technique are fullerene-like (IF) nanoparticles which are either organic or inorganic and organic nanotubes such as carbon nanotubes. Terms such as "inorganic fullerene-like (IF) particles" and "inorganic fullerene-like (IF) nanoparticles" used within the context of the specification of the disclosed technique include hollow and non-hollow nanoparticles of transition metal chalcogenides and dichalcogenides, made up of single layers or multi-layers and having structures such as spheres, tubes, nested polyhedra, onion-like and the like. A "chalcogen" as used herein refers to any one of the following elements: S (sulfur), Se (selenium) or Te (tellurium). The metal chalcogenides and dichalcogenides are preferably selected from $TiS_2$, $TiSe_2$, $TiTe_2$, $WS_2$, $WSe_2$, $WTe_2$, $MOS_2$, $MoSe_2$, $MoTe_2$, $SnS_2$, $SnSe_2$, $SnTe_2$, $RuS_2$, $RuSe_2$, $RuTe_2$, GaS, GaSe, GaTe, InS, InSe, $HfS_2$, $ZrS_2$, $VS_2$, $ReS_2$ and $NbS_2$. More preferably, the metal chalcogenides and dichalcogenides are selected from $WS_2$ and $MoS_2$.

Molybdenum disulfide, tungsten disulfide and graphite are currently used in industrial, manufacturing, mining, marine, agriculture and automotive applications to reduce friction and wear. Tungsten disulfide ($WS_2$) is a dry-film lubricant that was developed for NASA by Stanford University in the 1960s. Following its initial debut, tungsten disulfide found its way into industrial applications, primarily in aerospace and defense applications. Tungsten disulfide is known to improve wear properties and to enhance lubricity. When applied to a substrate material, tungsten disulfide forms a very thin layer due to the fact that it does not bond to itself. As a result, the dimensions and tolerances of treated parts are not compromised or appreciably affected when a substrate is treated with tungsten disulfide.

U.S. Pat. No. 6,390,992 to Morris et al., entitled "Intraluminal device with lubricious surface" describes a guidewire with a tenacious lubricious coating on its surface comprising finely divided lubricious particulate selected from the group consisting of tungsten disulfide, molybdenum disulfide and the like. Tungsten disulfide or molybdenum disulfide are applied as a surface treatment in order to provide lubricious properties to the guidewire. As stated above, surface treatment provides a film that tends to be unstable and break off from the joint implant.

According to the disclosed technique a matrix prepared from a polymer such as UHMWPE with nanotube nanoparticles of tungsten disulfide ($WS_2$), for example, forms a matrix possessing superior wear resistant properties. The mechanism of such a matrix formed from polymer and nanotube nanoparticles appears to be somewhat similar to that of high tin bronze alloys which are stronger and have a high wear resistance and low friction resistance than plain bronze. The rolling friction is the force resisting the motion when a body (such as a ball, tire, or wheel) rolls on a surface. With respect to joint implants such as hip replacement implant 10 (shown in FIG. 1), head 14 moves within a cup-shaped depression of liner 12 which fits into cup 11. If, for example, liner 12 is replaced with a polymeric liner according to the disclosed technique, the circular/rotational movement of the nanoparticles within the matrix in response to the forces transmitted in hip replacement implant 10, will reduce the rolling friction in the implant, thereby enhancing the wear resistance of the prosthesis.

The disclosed technique provides a polymeric liner for use in joint implants such as a hip joint, a knee joint, an ankle joint, an intervertebral disc, a shoulder joint, an elbow joint, a wrist joint, a finger joint, a finger metacarpal joint, a toe joint, a toe-metatarsal joint, a carpometacarpal joint and the like. The polymeric liner is prepared from a polymeric matrix including a polymeric material and at least one nanotube nanoparticle. The polymeric material may be selected from crosslinked or uncrosslinked UHMWPE, PEEK, carbon fiber-reinforced PEEK or polyimides (PI). However, any other known polymeric material currently used in the production of liners can be used in the preparation of the polymeric liner disclosed herein.

According to the disclosed technique, the polymeric matrix comprises at least one nanotube nanoparticle having a volume concentration of between 5%-99% volume per volume. Preferably, the nanotube nanoparticles are selected from organic or inorganic fullerenes. An embodiment of the disclosed technique includes nanotube nanoparticles such as inorganic IF particles and inorganic IF nanoparticles selected from the list consisting of: $TiS_2$, $TiSe_2$, $TiTe_2$, $WS_2$, $WSe_2$, $WTe_2$, $MoS_2$, $MoSe_2$, $MoTe_2$, $SnS_2$, $SnSe_2$, $SnTe_2$, $RuS_2$, $RuSe_2$, $RuTe_2$, GaS, GaSe, GaTe, InS, InSe, $HfS_2$, $ZrS_2$, $VS_2$, $ReS_2$ and $NbS_2$. More preferably, the nanoparticles are selected from $WS_2$, $MoS_2$ or any other organic or inorganic nanotube particle.

Figure 5:
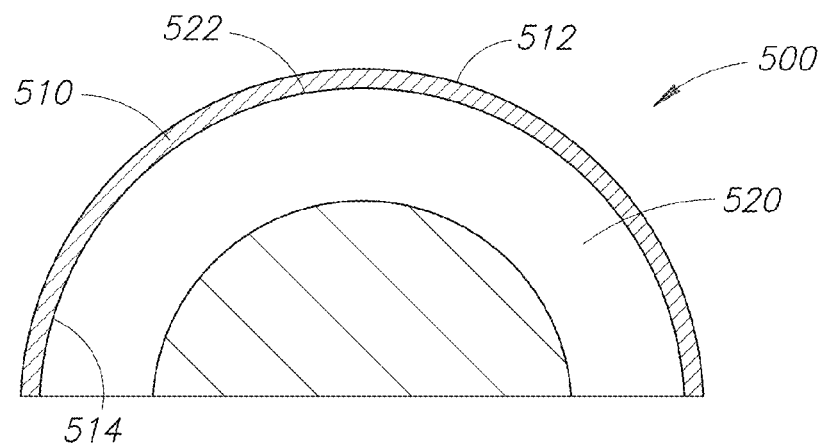
FIG. 5 is a cross-sectional side view of a first polymeric liner, constructed and operative in accordance with an embodiment of the disclosed technique.

Reference is now made to FIG. 5 which is a cross-sectional side view of a first polymeric liner, generally referenced 500, constructed and operative in accordance with an embodiment of the disclosed technique. Polymeric liner 500 includes a friction reducing member 510 and a body member 520. For example, polymeric liner 500 can be applied instead of prior art liners, such as liners 12, 22, 32 and 42 (see FIGS. 1-4). Friction reducing member 510 comprises an outer surface 512 and an inner surface 514. Friction reducing member 510 is produced from a polymeric matrix including a polymeric material and at least one nanotube nanoparticle having a volume concentration of between 5%-99% v/v. Preferably, the polymeric material is selected from UHMWPE, PEEK, carbon fiber-reinforced PEEK or PI. However, any other known polymeric material currently used in the production of liners can be used. The polymeric matrix in several embodiments of the disclosed technique may include at least one nanotube nanoparticle in different volumes of concentration, such as 70%-90% v/v, 60%-90% v/v, 40%-70% v/v or 5%-50% v/v. In these embodiments, the nanotube nanoparticle should have a volume concentration of 10%-80% v/v, however other volume concentrations are possible as listed above. Preferable nanotube nanoparticles are inorganic fullerene-like (IF) particles and inorganic fullerene-like (IF) nanoparticles selected from $TiS_2$, $TiSe_2$, $TiTe_2$, $WS_2$, $WSe_2$, $WTe_2$, $MoS_2$, $MoSe_2$, $MoTe_2$, $SnS_2$, $SnSe_2$, $SnTe_2$, $RuS_2$, $RuSe_2$, $RuTe_2$, GaS, GaSe, GaTe, InS, InSe, $HfS_2$, $ZrS_2$, $VS_2$, $ReS_2$ and $NbS_2$. More preferably, the nanotube nanoparticles are selected from $WS_2$ and $MoS_2$. Friction reducing member 510 may have a mean depth or thickness in the range 0.2 to 1.0 millimeters (herein abbreviated mm) although other mean depths or thicknesses are possible.

Preferably the dimensions of the friction reducing member are 3%-50% of the total mean depth (i.e., thickness) of the polymeric liner. More preferably, the mean depth of the friction reducing member is about 5% of the total mean depth of the polymeric liner. For example, a polymeric liner for a total hip replacement will have a friction reducing member having a mean depth or thickness in the range of 24-28 mm and a body member with a mean depth or thickness in the range of 38-50 mm.

Body member 520 has at least one inner surface (referenced 522 in FIG. 5). Inner surface 522 of body member 520 is conjoined with inner surface 514 of friction reduction member 510. Body member 520 can be manufactured from any polymeric material currently used in the production of liners. Preferably, body member 520 is produced from a polymer selected from UHMWPE, PEEK, carbon fiber-reinforced PEEK or PI.

Figure 6:
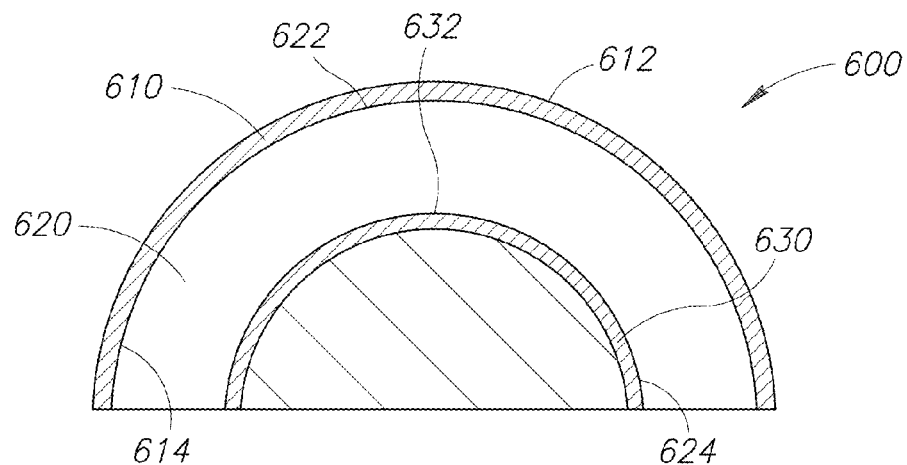
FIG. 6 is a cross-sectional side view of a second polymeric liner, constructed and operative in accordance with another embodiment of the disclosed technique.

Reference is now made to FIG. 6 which is a cross-sectional side view of a second polymeric liner, generally referenced 600, constructed and operative in accordance with another embodiment of the disclosed technique. Polymeric liner 600 includes three layers: a first friction reducing member 610, a body member 620 and a second friction reducing member 630. To ease understanding reducing member 610 may be referred to as a "first layer" or "layer one," body member 620 may be referred to as a "second layer" or "layer two" and friction reducing member 630 may be referred to as a "third layer" or "layer three." First and second friction reducing members 610 and 630 are produced from the same polymeric matrix as friction reducing member 510 (FIG. 5). Body member 620 is produced from the same material used for the preparation of body member 520. First friction reducing member 610 comprises an outer surface 612 and an inner surface 614. Second friction reducing member 630 comprises an inner surface 632. Body member 620 includes first inner surface 622 and second inner surface 624. When all layers are conjoined, body member 620 is sandwiched between first friction reducing member 610 and second friction reducing member 630 such that first inner surface 622 of body member 620 is conjoined with inner surface 614 of friction reduction member 610. Similarly, second inner surface 624 is conjoined with inner surface 632 of second friction reducing member 630.

Figure 7:
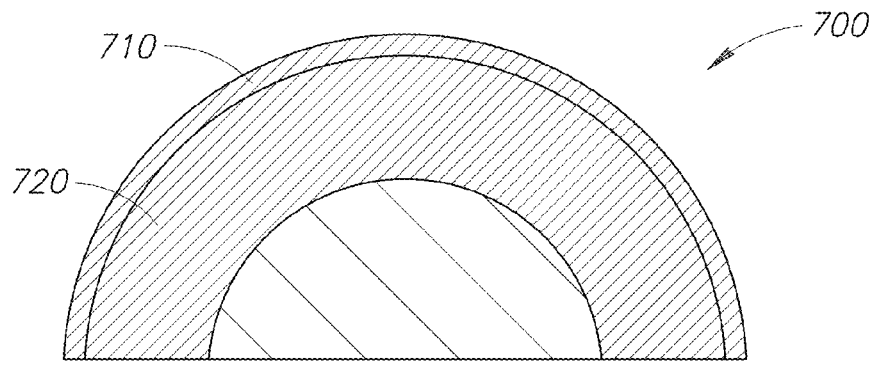
FIG. 7 is a cross-sectional side view of a third polymeric liner, constructed and operative in accordance with a further embodiment of the disclosed technique.

Reference is now made to FIG. 7 which is a cross-sectional side view of a third polymeric liner, generally referenced 700, constructed and operative in accordance with a further embodiment of the disclosed technique. Polymeric liner 700 includes a friction reducing member 710 and a body member 720, both made of a polymeric material and at least one nanotube nanoparticle having a volume concentration of between 5%-99% v/v. Being made of the same composition it is not possible to differentiate in FIG. 7 between the two members. The resulting polymeric liner is composed of substantially uniformly distributed nanotube nanoparticles in a polymeric matrix. Alternatively, it is also possible to produce a liner having a varying distribution of the nanotube nanoparticles by applying magnetic and/or electric fields to the polymeric liner during production. For example, in an embodiment of the disclosed technique, the polymeric liner is manufactured such that the density of the nanotube nanoparticles is higher on the outer surface of polymeric liner 700 than the density in body member 720, i.e., density decreases with depth. This can be achieved similarly with the embodiments shown in FIGS. 5 and 6, with the density of the nanoparticles in friction reducing members 510 (FIG. 5), 610 and 630 (both from FIG. 6) being higher than the density of nanoparticles in the body members 520 (FIG. 5) and 620 (FIG. 6). Optionally, the density of the nanoparticles can vary as a function of the distance from the center of the polymeric liner. For example, the density of the nanoparticles on the outer surface of the liner can be around 99% whereas the density in the center of the liner can vary between 5%-50%.

Figure 8:
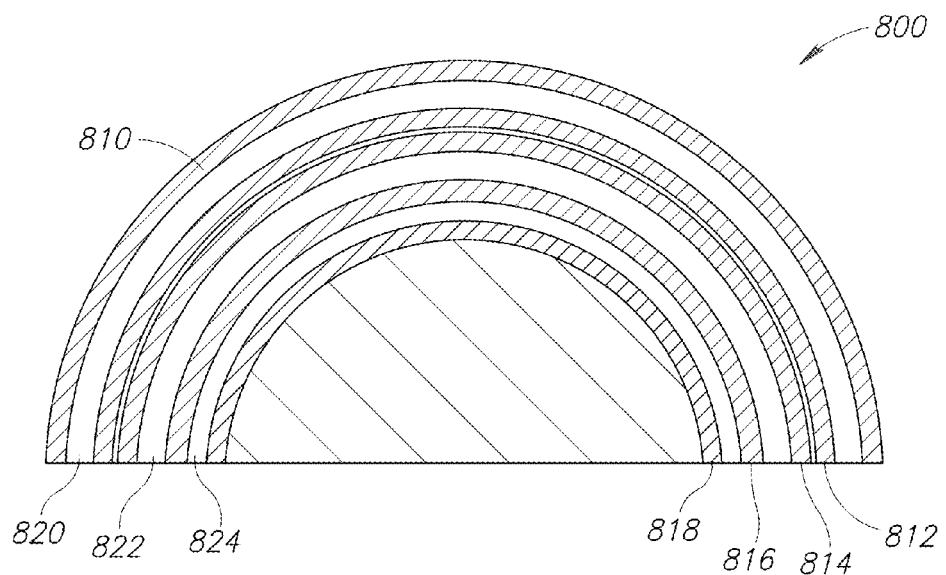
FIG. 8 is a cross-sectional side view of a fourth polymeric liner, constructed and operative in accordance with another embodiment of the disclosed technique.

Reference is now made to FIG. 8 which is a cross-sectional side view of a fourth polymeric liner, generally referenced 800, constructed and operative in accordance with another embodiment of the disclosed technique. Polymeric liner 800 includes a plurality of friction reducing members 810, 812, 814, 816 and 818 and a plurality of body members 820, 828 and 824. The body members are placed one on top of the other such that friction reducing member 810 forms one (outer skin) contacting surface and friction reducing member 818 forms another (inner skin) contacting surface of polymeric liner 800. Friction reducing members 812-816 are interspersed between body members 820-824 as shown in FIG. 8. It would be appreciated that the plurality of friction reducing members and the plurality of body members are conjoined in a similar manner as illustrated in detail with respect of FIGS. 5 and 6 whereas an inner surface of one member is conjoined with an outer surface of another member.

Figure 9:
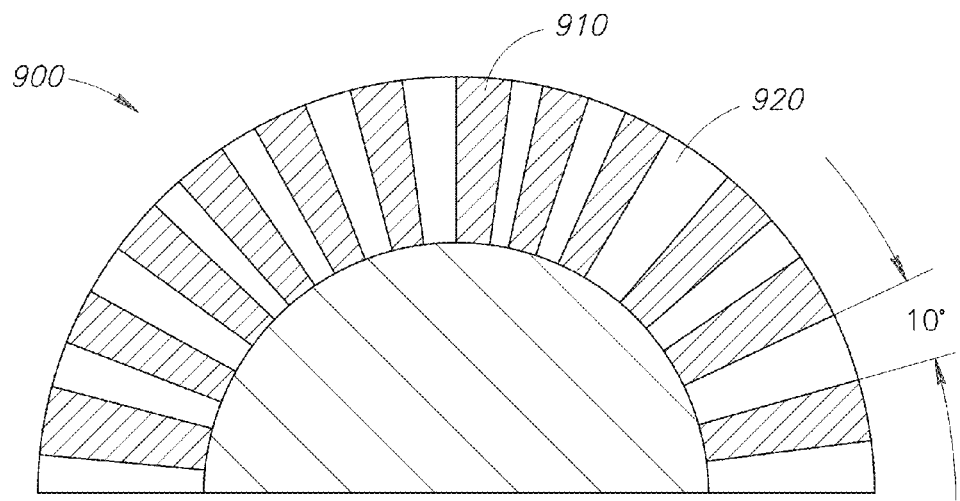
FIG. 9 is a cross-sectional side view of a fifth polymeric liner, constructed and operative in accordance with a further embodiment of the disclosed technique.

Reference is now made to FIG. 9 which is a cross-sectional side view of a fifth polymeric liner, generally referenced 900, constructed and operative in accordance with a further embodiment of the disclosed technique. As shown, polymeric liner 900 is assembled from vertically positioned friction reducing members 910 and body members 920. In this specific embodiment the body members and friction reducing members are made of pre-preg carbon fiber-reinforced PEEK which undergo compression molding so that all members are conjoined.

Figure 10:
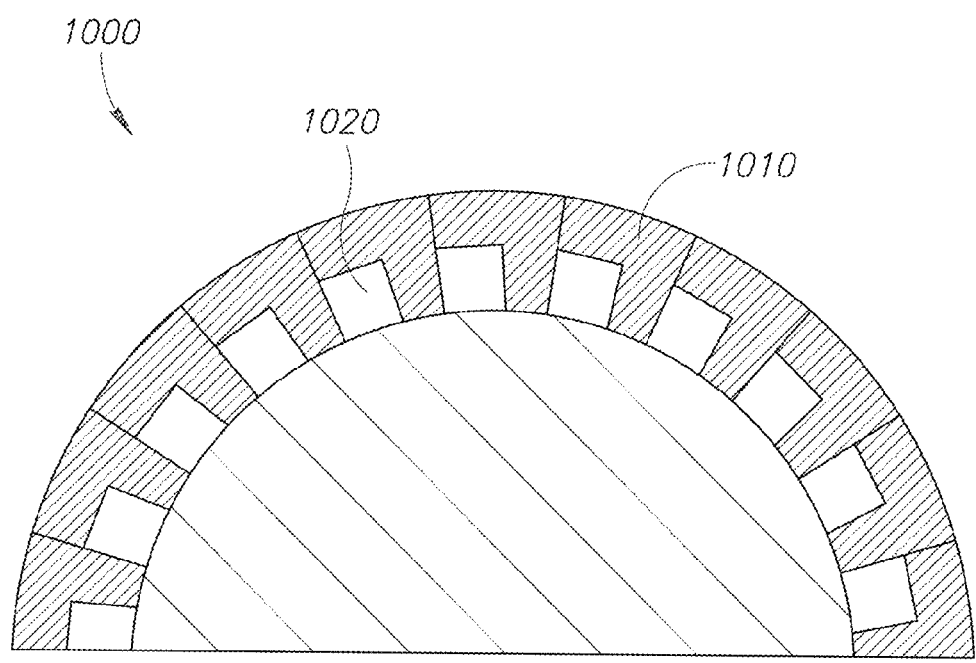
FIG. 10 is a cross-sectional side view of a sixth polymeric liner, constructed and operative in accordance with a further embodiment of the disclosed technique.

FIG. 10 is a cross-sectional side view of a sixth polymeric liner, generally referenced 1000, constructed and operative in accordance with a further embodiment of the disclosed technique. Polymeric liner 1000 is assembled from a plurality of L-shaped sections of friction reducing members 1010 constructed to be interjoined with a plurality of body members 1020 to result in the desired structure of the polymeric liner.

It will be appreciated that any other combination of complementing structures can be used for the construction of the polymeric liner and that the embodiment shown in FIG. 10 is only one example for a combination of a plurality of different possible structural constructions of the friction reducing members, body members and a combination thereof which can form the polymeric liner.

As stated above, the friction reducing member and the body member are conjoined preferably by compression molding. However, any other method of coupling such as mold injection, 3D printing, adhesion or any other suitable method can be applied. By way of example, the following is a method for preparing a polymeric liner for medical joint implants by compression molding in accordance with an embodiment of the disclosed technique. The method comprises the following: providing a mold with a cavity in a shape of the polymeric liner. For example, the cavity in the mold can be designed to form the polymeric liner shown in FIG. 1 as liner 12. Then, applying a first layer made of a polymeric matrix in the cavity of the mold, wherein the first layer contains a polymeric material and at least one nanotube nanoparticle having a volume concentration of between 5-99% V/V. This first layer forms the friction reducing member, referenced as 510 in FIG. 5. Thereafter, a second layer of a polymeric material is applied on the first layer of the polymeric matrix. The second layer forms a body member made of a polymeric material, referenced as 520 in FIG. 5. The mold is closed and heated with the polymeric material to a temperature below the melting point of the polymeric material. Pressure is applied to the mold such that air contained in the mold is sucked out and the polymeric material forms in the shape of the polymeric liner. The final procedure is opening the mold and removing the polymeric liner from the mold. The resulting polymeric liner comprises a friction reducing member and a body member which are conjoined by compression molding.

In an embodiment of the disclosed method of production, before the procedure of closing the mold, a third layer of polymeric matrix is applied to the second layer. This third layer contains a polymeric material and at least one nanotube nanoparticle having a volume concentration of between 5%-99% v/v. The resulting polymeric liner according to this embodiment is composed of a skin made of homogeneously distributed nanoparticles in a polymeric matrix and a body member made of a polymeric material. Preferably, the resulting skin substantially covers the body member. In an additional embodiment of the disclosed method of production, the nanotube nanoparticle is selected from nanoparticles of tungsten disulfide ($WS_2$) and molybdenum disulfide ($MoS_2$) having a volume concentration of between 5%-99% v/v.

A further embodiment of the disclosed method of production includes the procedures of providing a mold with a cavity in a shape of the polymeric liner and thereafter, loading a required amount of a polymeric matrix into the cavity, wherein the polymeric matrix includes a polymeric material and a nanotube nanoparticle having a volume concentration of between 5%-99% v/v. The mold with the polymeric matrix is then heated to a temperature below the melting point of the polymeric material. Pressure is applied to the mold such that air contained in the mold is sucked out and the polymeric material forms in the shape of the polymeric liner. The final procedure is opening the mold and removing the polymeric liner from the mold. The resulting polymeric liner is composed of substantially uniformly distributed nanotube nanoparticles in a polymeric matrix.

The polymer is provided as a powder or grinded material. The polymer is then mixed with the nanotube nanoparticles and the mixture is transferred into a mold. The temperature and pressure of the mold determine the melting and cooling of the polymeric material in the mold. Both temperature and pressure can be controlled and revised to accord with the specific melting temperature and solidification time required for the specific material. With respect to the concentration gradient of the nanoparticles, this can be controlled by an electric or magnetic field which can be formed during the stages of preparation of the polymeric liner. The electric or magnetic field will determine the concentration of the nano-particle on a specific surface/layer and the viscosity of the polymer is determined by temperature and time.

It will be appreciated by persons skilled in the art that the disclosed technique is not limited to what has been particularly shown and described hereinabove. Rather the scope of the disclosed technique is defined only by the claims, which follow.

The invention claimed is:

1. A polymeric liner for a medical joint implant, comprising:
   at least one friction reducing member having at least one outer surface and at least one inner surface, and
   at least one body member having at least one inner surface in contact with said at least one friction reducing member inner surface, wherein said at least one body member and said at least one friction reducing member are separate components, wherein at least one of said at least one friction reducing member is positioned on a surface area of said polymeric liner, said surface area contacts a moving part of said medical joint implant; and
   wherein said at least one friction reducing member and said at least one body member are prepared from a polymeric matrix comprising a polymeric material and at least one metal chalcogenides or dichalcogenides nanoparticle,
   wherein said at least one metal chalcogenides or dichalcogenides nanoparticle is distributed within said polymeric matrix, and
   wherein said at least one metal chalcogenides or dichalcogenides nanoparticle is selected from the group consisting of: nanotubes nanoparticles of tungsten disulfide ($WS_2$); and molybdenum disulfide ($MoS_2$).

2. The polymeric liner according to claim 1, wherein said at least one friction reducing member forms an outer skin of said polymeric matrix, thereby substantially covering said at least one body member.

3. The polymeric liner according to claim 1, wherein said at least one body member is produced from UHMWPE.

4. The polymeric liner according to claim 1, wherein said at least one friction reducing member is produced from a polymeric matrix and at least one metal chalcogenides or dichalcogenides nanotube nanoparticle in different volumes of concentration selected from the group consisting of:
   a. 70%-99% v/v,
   b. 60%-90% v/v,
   c. 40%-70% v/v, or
   d. 5%-50% v/v.

5. The polymeric liner according to claim 1, wherein said at least one body member and said at least one friction reducing member are conjoined by compression molding.

6. A polymeric liner for a medical joint implant, comprising:
   at least one friction reducing member having at least one outer surface and at least one inner surface, and
   at least one body member having at least one inner surface in contact with said at least one friction reducing member inner surface, wherein said at least one body member and said at least one friction reducing member are separate components, wherein at least one of said at least one friction reducing member is positioned on a surface area of said polymeric liner, said surface area contacts a moving part of said medical joint implant;
   wherein said at least one friction reducing member and said at least one body member are is produced from a polymeric matrix comprising a polymeric material and at least one metal chalcogenides or dichalcogenides nanotube nanoparticle in different volumes of concentration selected from the list consisting of:
   70%-99% v/v,
   60% 90% v/v,
   40% 70% v/v, or
   5% 50% v/v,
   wherein said at least one metal chalcogenides or dichalcogenides nanoparticle is distributed within said polymeric matrix, wherein said at least one metal chalcogenides or dichalcogenides nanoparticle is selected from the group consisting of: nanotubes nano articles of tungsten disulfide ($WS_2$); and molybdenum disulfide ($MoS_2$).

7. The polymeric liner according to claim 6, wherein said at least one friction reducing member forms an outer skin of said polymeric matrix, thereby substantially covering said at least one body member.

8. The polymeric liner according to claim 6, wherein said at least one body member is produced from UHMWPE.

9. The polymeric liner according to claim 6, wherein said at least one body member and said at least one friction reducing member are conjoined by compression molding.

10. The polymeric liner according to claim 6, wherein said polymeric matrix having a volume concentration of between 5%-99% volume per volume (v/v) of said polymeric material.

11. The polymeric liner according to claim 6, wherein said polymeric matrix having a volume concentration of between 1%-5% volume per volume (v/v) of said at least one metal chalcogenides or dichalcogenides nanoparticle.

12. The polymeric liner according to claim 6, wherein said at least one friction reducing member and said at least one body member are produced from UHMWPE.

* * * * *